(12) United States Patent
Garner et al.

(10) Patent No.: US 7,580,748 B2
(45) Date of Patent: Aug. 25, 2009

(54) HEART STIMULATOR

(75) Inventors: Garth Garner, Tigard, OR (US); Hannes Kraetschmer, West Linn, OR (US); Dirk Muessig, West Linn, OR (US); Indra B. Nigam, Tigard, OR (US)

(73) Assignee: Biotronik CRM Patent AG, Baar (CH)

( * ) Notice: Subject to any disclaimer, the term of this patent is extended or adjusted under 35 U.S.C. 154(b) by 321 days.

(21) Appl. No.: 11/567,753

(22) Filed: Dec. 7, 2006

(65) Prior Publication Data

US 2008/0140146 A1    Jun. 12, 2008

(51) Int. Cl.
*A61N 1/00* (2006.01)
(52) U.S. Cl. ....................................................... 607/27
(58) Field of Classification Search .................. 607/9, 607/27, 28
See application file for complete search history.

(56) References Cited

U.S. PATENT DOCUMENTS 6,584,354 B1 *   6/2003   Mann et al. ................... 607/28
6,973,350 B1 *  12/2005   Levine et al. ................. 607/27

* cited by examiner

*Primary Examiner*—Scott M Getzow
(74) *Attorney, Agent, or Firm*—Dalina Law Group, P.C.

(57) ABSTRACT

A heart stimulator provides a reliable automatic capture threshold search feature. A stimulation pulse generator is connected to at least a ventricular stimulation electrode for delivering electric stimulation pulses to at least the ventricle of the heart. The stimulation pulses generated have a strength depending on a control signal. A sensing stage is connected to an electrode for picking up electric potentials inside at least said ventricle of a heart and a control unit connected to the sensing stage and to the stimulation pulse generator determines points of time for scheduling stimulation pulses, to trigger the stimulation pulse generator so as to deliver a stimulation pulse when scheduled and to put out control signals for controlling the strength of the stimulation pulse. The control unit is further adapted to perform a capture analysis which may take into account extraordinary events.

19 Claims, 4 Drawing Sheets

HEART STIMULATOR

BACKGROUND OF THE INVENTION

1. Field of the Invention

The invention refers to a heart stimulator for stimulating at least one chamber of a heart by means of electrical stimulation pulses. The invention particularly refers to implantable pacemakers and implantable cardioverter/defibrillators featuring automatic capture threshold search.

2. Description of the Related Art

Implantable heart stimulators can be used for treating a variety of heart disorders like bradycardia, tachycardia or fibrillation by way of electric stimulation pulses delivered to the heart tissue, the myocardium. In order to be effective, a stimulation pulse needs to have strong enough of a strength to excite the myocardium of the heart chamber to be paced. Excitation of the myocardium that in turn is followed by a contraction of the respective heart chamber. The stimulation pulse strength high enough to cause excitation of the myocardium is called capture threshold since strong enough a stimulation pulse causes capture.

Depending on the disorder to be treated, such heart stimulator generates electrical stimulation pulses that are delivered to the heart tissue (myocardium) of a respective heart chamber according to an adequate timing regime. Delivery of stimulation pulses to the myocardium is usually achieved by means of an electrode lead that is electrically connected to a stimulation pulse generator inside a heart stimulator's housing and that carries a stimulation electrode in the region of its distal end. A stimulation pulse also is called a pace. Similarly, pacing a heart chamber means stimulating a heart chamber by delivery of a stimulation pulse.

In order to be able to sense a contraction a heart chamber that naturally occurs without artificial stimulation and that is called intrinsic, the heart stimulator usually comprises at least one sensing stage that is connected to a sensing electrode on the electrode placed in the heart chamber. An intrinsic excitation of a heart chamber results in characteristic electrical potentials that can be picked up via the sensing electrode and that can be evaluated by the sensing stage in order to determine whether an intrinsic excitation (called an intrinsic event), has occurred.

Usually, a heart stimulator features separate stimulation generators for each heart chamber to be stimulated. Therefore, in a dual chamber pacemaker, usually an atrial and a ventricular stimulation pulse generator for generating atrial and ventricular stimulation pulses are provided. Delivery of an atrial or a ventricular stimulation pulse causing an artificial excitation of the atrium or the ventricle, respectively, is called an atrial stimulation event AP (atrial paced event) or a ventricular stimulation event VP (ventricular paced event), respectively. The strength of stimulation pulses delivered by the respective stimulation pulse generator is adjustable in order to be able to adjust the stimulation pulse strength to be just sufficient to cause capture (above capture threshold) and thus using as little energy as possible to be effective. Stimulation pulse strength depends on both, duration and amplitude of the stimulation pulse. Thus, stimulation pulse strength can be adjusted by varying pulse duration, pulse amplitude or both. Usually, pulse strength is adjusted by altering the pulse amplitude.

Common heart stimulators feature separate sensing stages for each heart chamber to be of interest. In a dual chamber pacemaker usually two separate sensing stages, an atrial sensing stage and a ventricular sensing stage, are provided that are capable to detect intrinsic atrial events AS (atrial sensed event) or intrinsic ventricular events $V_S$ (ventricular sensed event), respectively.

As known in the art, separate sensing and pacing stages are provided for three-chamber (right atrium RA, right ventricle RV, left ventricle LV) or four-chamber (right atrium RA, left atrium LA, right ventricle RV, left ventricle LV) pacemakers or ICDs.

By means of a sensing stage for a heart chamber to be stimulated, the pacemaker is able to only trigger stimulation pulses when needed that is when no intrinsic excitation of the heart chamber occurs in time. Such mode of pacing a heart chamber is called demand mode. In the demand mode the pacemaker schedules an atrial or a ventricular escape interval that causes triggering of an atrial or ventricular stimulation pulse when the escape interval times out. Otherwise, if an intrinsic atrial or ventricular event is detected prior to time out of the respective atrial or ventricular escape interval, triggering of the atrial or ventricular stimulation pulse is inhibited. Such intrinsic (natural, non-stimulated) excitation are manifested by the occurrence of recognizable electrical signals that accompany the depolarization or excitation of a cardiac muscle tissue (myocardium). The depolarization of the myocardium is usually immediately followed by a cardiac contraction. For the purpose of the present application, depolarization and contraction may be considered as simultaneous events and the terms "depolarization" and "contraction" are used herein as synonyms. The recognizable electrical signals that accompany the depolarization or excitation of a heart chamber are picked up (sensed) by the atrial or the ventricular sensing channel, respectively. Thus, by means of the sensing stages, intracardiac electrogram (IEGM) signals are acquired, that can be evaluated by the heart stimulator. Simple evaluation only checks whether the IEGM exceeds a given threshold in order to detect a sense event. More complex evaluation includes analysis of the IEGM's morphology.

In heart cycle, an excitation of the myocardium leads to depolarization of the myocardium that causes a contraction of the heart chamber. If the myocardium is fully depolarized it is unsusceptible for further excitation and thus refractory. Thereafter, the myocardium repolarizes and thus relaxes and the heart chamber is expanding again. In a typical electrogram (EGM) depolarization of the ventricle corresponds to a signal known as "R-wave". The repolarization of the ventricular myocardium coincides with a signal known as "T-wave". Atrial depolarization is manifested by a signal known as "P-wave".

A natural contraction of a heart chamber thus can be detected by evaluating electrical signals sensed by the sensing channels. In the sensed electrical signal the depolarization of an atrium muscle tissue is manifested by occurrence of a P-wave. Similarly, the depolarization of ventricular muscle tissue is manifested by the occurrence of an R-wave. A P-wave or an R-wave thus leads to an atrial sense event As or a ventricular sense event Vs, respectively.

Picking up and evaluating electric signals in a heart chamber by a sensing stage also is used to control effectiveness of a stimulation pulse as pointed out in further detail below.

Automatic capture threshold search serves for determining an optimum stimulation pulse strength that is just sufficient to capture the heart tissue and that does not include an excessive safety margin. Furthermore, some devices include an automatic capture control feature, which checks whether or not a delivered pace pulse has resulted in capture of the heart tissue on a beat-to-beat basis and adjust the pace energy as warranted by the situation—with this feature active, the safety margin can be further reduced.

Several modes of operation are available in a state of the art multi mode pacemaker. The pacing modes of a pacemaker, both single and dual or more chamber pacemakers are classified by type according to a three letter code. In such code, the first letter identifies the chamber of the heart that is paced (i.e., that chamber where a stimulation pulse is delivered), with a "V" indicating the ventricle, an "A" indicating the atrium, and a "D" indicating both the atrium and ventricle. The second letter of the code identifies the chamber wherein cardiac activity is sensed, using the same letters, and wherein an "O" indicates no sensing occurs. The third letter of the code identifies the action or response that is taken by the pacemaker. In general, three types of action or responses are recognized: (1) an Inhibiting ("I") response wherein a stimulation pulse is delivered to the designated chamber at the conclusion of the appropriate escape interval unless cardiac activity is sensed during the escape interval, in which case the stimulation pulse is inhibited; (2) a Trigger ("T") response wherein a stimulation pulse to a prescribed chamber of the heart a prescribed period of time after a sensed event; or (3) a Dual ("D") response wherein both the Inhibiting mode and Trigger mode may be evoked, e.g., with the "inhibiting" occurring in one chamber of the heart and the "triggering" in the other.

To such three letter code, a fourth letter "R" may be added to designate a rate-responsive pace-maker and/or whether the rate-responsive features of such a rate-responsive pacemaker are enabled ("O" typically being used to designate that rate-responsive operation has been disabled). A rate-responsive pacemaker is one wherein a specified parameter or combination of parameters, such as physical activity, the amount of oxygen in the blood, the temperature of the blood, etc., is sensed with an appropriate sensor and is used as a physiological indicator of what the pacing rate should be. When enabled, such rate-responsive pacemaker thus provides stimulation pulses that best meet the physiological demands of the patient.

A dual chamber pacemaker featuring an atrial and a ventricular sensing stage and an atrial and a ventricular stimulation pulse generator can be operated in a number of stimulation modes like VVI, wherein atrial sense events are ignored and no atrial stimulation pulses are generated, but only ventricular stimulation pulses are delivered in a demand mode, AAI, wherein ventricular sense events are ignored and no ventricular stimulation pulses are generated, but only atrial stimulation pulses are delivered in a demand mode, or DDD, wherein both, atrial and ventricular stimulation pulses are delivered in a demand mode. In such DDD mode of pacing, ventricular stimulation pulses can be generated in synchrony with sensed intrinsic atrial events and thus in synchrony with an intrinsic atrial rate, wherein a ventricular stimulation pulse is scheduled to follow an intrinsic atrial contraction after an appropriate atrioventricular delay (AV-delay; AVD), thereby maintaining the hemodynamic benefit of atrioventricular synchrony.

The energy needed for a stimulation pulse is delivered by a depletable battery that cannot easily be exchanged. Therefore the energy used for a stimulation pulse shall be a little as possible without affecting effectiveness of the stimulation pulse.

A stimulation pulse to the myocardium only effectively excites the myocardium and thus causes capture of a respective heart chamber, if the myocardium of that chamber is not in a refractory state and if the stimulation pulse strength is above the capture threshold of the myocardium. A sub-threshold stimulation pulse will not cause capture even if delivered to the myocardium in its non-refractory state. Capture only occurs if a stimulation pulse is strong enough to cause excitation of the myocardium. Pulse strength depends both on duration and amplitude of an electrical stimulation pulse. Usually, stimulation pulse strength is adjusted by adjusting the pulse amplitude while maintaining the pulse duration.

It is desirable to adjust the stimulation pulse strength so that the stimulation pulse strengths for particular heart chambers just above capture threshold in order to spend as little energy as possible for a single stimulation pulse while ensuring reliable effectiveness of a stimulation pulse delivered.

Since capture threshold may vary from heart chamber to heart chamber and from patient to patient and may even vary over time, there is a need for automatic capture testing and determination in particular as far as implantable heart stimulators are concerned.

In order to determine whether a stimulation pulse has let to capture or not, modern heart stimulators provide for an automatic capture threshold search and/or automatic capture control after delivery of a stimulation pulse.

During automatic capture threshold search stimulation pulses of different strength are tested—at least once daily—in order to determine individual capture threshold to which only a small safety margin needs to be added. With heart stimulators that include an automatic capture control feature, which checks whether or not a delivered pace pulse has resulted in capture of the heart tissue on a beat-to-beat basis it is possible to adjust the stimulation pulse strength as warranted by the situation. With this feature active, the safety margin can be further reduced.

Both of the features mentioned above, i.e. the automatic capture threshold search and the automatic capture control may be based on analyzing the post-pace artifact in the EGM signal. Basically, a capture event is identified when the post-pace artifact deviates from the known non-capture artifact by a significant amount for one or more characteristics of the waveform.

In some cases a stimulated excitation occurs simultaneously with an intrinsic excitation and causes a so-called fusion beat. It should be noted that a fusion beat can result in incorrect conclusions—the event may be classified as a capture or as a non-capture depending upon, and not limited to, the timing of the intrinsic beat and the pace delivery.

From the above it becomes clear that evaluation of the post-pace artifact to conclude whether or not the pace pulse has resulted in a capture may produce unreliable results due to fusion beats. This unreliability in capture classification (CC) has the potential of producing a few undesirable wrong conclusions. During an automatic capture threshold search (CTS) in the ventricle, an incorrect non-capture classification that may be due to a fusion beat can lead to a determination of the capture threshold as being higher than what it really is. During automatic capture control (ACC), incorrect non-capture classifications may lead to unnecessary backup pace pulses and/or unnecessary initiations of CTS.

The problem of fusion beats and they are to be avoided be adapting a programmable AV-delay is illustrated in EP 0 600 631.

While performing a capture threshold search in the ventricle with the bradycardia support mode programmed to be atrium-synchronous, e.g. DDD, fusion beats in the ventricle can be avoided by programming an AV-delay that is short enough to ensure that the ventricular stimulation pulse—having a pulse strength to be tested—is delivered well before any conducted intrinsic event can occur in the ventricle. In normal cases, this approach results in reliable capture classifications by analyzing the post-pace artifact in the EGM signal.

There is, however, a possibility that a premature atrial contraction (PAC) may result in a conducted ventricular depolarization right before or at the same time as the ventricular stimulation pulse having a pulse strength to be tested is delivered—and this fusion beat, as described earlier, may cause an incorrect capture classification. In case of an incorrect non-capture classification, this can ultimately lead to determination of the capture threshold being higher than what it really is; in some cases, the CTS may take too long time and may timeout resulting in a failed test.

For the purpose of this disclosure, the following abbreviations are used are used:

| Abbreviation | Meaning |
|---|---|
| ACC | Automatic Capture Control |
| Ap | Atrial pace (stimulation) event |
| Ars | refractory atrial sense event |
| As | Atrial sense event |
| A | Any atrial event |
| AVD | AV delay as applied by the pacemaker (in contrast to intrinsic AV delay) |
| CC | Capture Classification |
| CRT | cardiac resynchronization therapy |
| CTS | automatic Capture Threshold Search |
| PAC | premature atrial contraction |
| PVARP | Post-ventricular atrial refractory period |
| VAI | VA interval (duration of the VA timer) |
| VES | Ventricular extra-systole |
| Vp | Ventricular pace (stimulation) event |
| Vs | Ventricular sense event |
| V | Any ventricular event |
| VT | Ventricular tachycardia |
| VF | ventricular fibrillation |

BRIEF SUMMARY OF THE INVENTION

It is an object of the invention to provide a heart stimulator that provides a reliable automatic capture threshold search feature.

According to the present invention the object of the invention is achieved by a heart stimulator featuring:

a stimulation pulse generator adapted to generate electric stimulation pulses and being connected or being connectable to at least a ventricular stimulation electrode for delivering electric stimulation pulses to at least a ventricle of the heart, the stimulation pulse generator being adapted to generate stimulation pulses having a strength depending an a control signal a sensing stage connected or being connectable to an electrode for picking up electric potentials inside at least the ventricle of a heart, the time course of the electric potentials representing a heart signal, and a control unit that is connected to the sensing stage and to the stimulation pulse generator.

The control unit is adapted to determine points of time for scheduling stimulation pulses, to trigger the stimulation pulse generator so as to deliver a stimulation pulse when scheduled and to put out control signals for controlling the strength of the stimulation pulse.

The control unit is further adapted to detect a stimulated excitation of a heart chamber after delivery of a stimulation pulse, the detection of stimulated excitation being carried out on the basis of the time course of electric potentials picked up by the sensing stage.

The control unit is further adapted to identify an extraordinary atrial event, such as a premature atrial contraction PAC, and to exclude the result of the capture detection based on the analysis of the next post-ventricular-pace artifact following such extraordinary atrial event from further evaluation.

According to a preferred embodiment, the control unit is adapted to carry out an automatic capture threshold search wherein ventricular stimulation pulses are delivered in an atrium synchronous stimulation mode using a shortened AV-delay being shorter than a natural atrioventricular conduction time. Capture or non-capture is detected by analyzing the post-pace artifact in the time course of electric potentials picked up by the sensing stage.

While using such shortened AV delay is always preferred with respect to automatic capture threshold search CTS, for the purpose of continuous automatic capture control ACC on a beat-to-beat basis pacing can be performed with any AV delay. In the ACC mode, fusion can cause a pace with a large enough pace amplitude to capture to look like non-capture. Therefore, during ACC mode it is preferred to modulate the AV Delay to confirm non-capture by ruling out the possibility of fusion. However, as an option the shortened AV delay can always be used use during ACC mode before deciding that the pace amplitude is not large enough to capture.

The invention is based on the insight that a premature atrial contraction (PAC) may result in a conducted ventricular depolarization right before or at the same time as the ventricular test energy stimulation pulse is delivered thus resulting in a fusion beat that may cause an incorrect capture classification, and that this problem can be avoided by identifying or, at least, suspecting presence of an extraordinary atrial event, such as a PAC, and excluding the result of the capture detection based the analysis of the next post-ventricular-pace artifact from further evaluation.

Alternatively, an entire capture threshold test or a portion of it, surrounding the newly found capture threshold could be repeated and only if the same or an almost same threshold is found again, it is confirmed. The disadvantage with this approach would be that one complete and one—at least— partial search will always be conducted and, for each case of a fusion beat resulting in incorrect threshold, one more—at least—partial search will be conducted.

According to a preferred embodiment, the control unit is adapted to identify potential extraordinary atrial events by counting all atrial events Ap, As, Ars, retrograde atrial sense events sense or PACs that follow a previous ventricular event and that precede the ventricular stimulation pulse that is subject of the capture analysis. In case of the counted number being more than one, a potential extraordinary atrial event is identified and the result of the capture analysis is not used.

Preferably, the control unit comprises a counter that counts all atrial events that follow the previous ventricular event and that precede the ventricular stimulation pulse that is subject of the capture analysis. In case of the counter value being more than one, the control unit excludes any result of the capture analysis based on a post-pace artifact that is caused by the ventricular stimulation pulse that follows a counter value of more than one. The counter is reset to zero with every ventricular event.

Thus, if an extraordinary atrial event is suspected, the result of the capture analysis is not used to affect the search process or lead to any determination of the capture threshold.

Preferably, the control unit is adapted to repeat delivery of a stimulation pulse having the same pulse strength as the stimulation pulse that has caused the post-pace artifact that is not considered due to an identified potential extraordinary atrial event.

Repetition of delivery of a stimulation pulse having the same pulse strength can be triggered at the end of either the ongoing or the next stimulated heart cycle. Such stimulation pulse having the same pulse strength as the stimulation pulse that was previously delivered is called repeated stimulation for the purpose of this disclosure.

According to a preferred embodiment, the control unit is adapted to ignore the result of the capture analysis for a ventricular stimulation pulse that follows a preceding atrial event with an AV-delay that is longer than a predetermined short AV-delay being shorter than a natural atrioventricular conduction time. The latter feature may be particularly advantageous in a heart stimulator wherein the control unit is adapted to carry out an automatic capture control on a beat-to-beat basis.

Such heart stimulator featuring automatic capture control ACC performs a capture analysis following each delivered ventricular pace pulse. In contrast to the CTS feature that is active for brief durations, e.g. once daily for a maximum of 2 minutes, the ACC feature is active on a beat-to-beat basis. A short AV delay attempted at avoiding fusion beats is not practical from the therapeutic point-of-view. The risk of fusion beats causing incorrect capture analysis is, therefore, higher for the ACC feature. Upon detecting a first non-capture, the control unit in its ACC mode of operation modulates the AV delay in an attempt to avoid fusion beats. In prior art heart stimulators in case of continued detection of non-capture in spite of the attempts to avoid fusion beats, a confirmed case of insufficient pace energy is declared—this may lead to either a disabling of the ACC feature or start of a new CTS.

Although performing ACC according to the prior art includes a state that uses a short AV delay, that ensures that the ventricular pace pulse is delivered well before any conducted intrinsic event can occur in the ventricle, this state is not used in case of unstable rhythms where excessive number of non-captures may have been seen at other used AV delays. According to the preferred embodiment of the invention a use of the state using the short AV delay is mandatory before deciding whether or not the pace energy is insufficient.

During all states of the ACC feature it is preferred to ignore results of capture analysis that follow potential extraordinary atrial events.

Accordingly, a heart stimulator is preferred that is capable to perform ACC on a beat-to-beat basis and that, in case of detection of non-capture, delivers backup stimulation pulses and that is capable to confirm whether or not the non-capture analysis is resulting from fusion beats, wherein the process of confirmation includes modulating the atrioventricular delay, and wherein the AV delay modulation scheme includes a step where the used atrioventricular delay is short enough to ensure that the preceding atrial event can not conduct down into the ventricle and cause a ventricular depolarization; and a declaration of insufficient energy in the stimulation pulse is made only when a non-capture conclusion is made using the a step of short atrioventricular delay.

A number of further problems and there solution shall be mentioned herein. The mentioned solutions can be implemented in a heart stimulator according to the invention thus leading to various preferred embodiments of the heart stimulator. Alternatively, the solutions can be implemented independently from each other thus representing independent inventions.

One further problem is related to triggering of ventricular stimulation pulses in Wenckebach mode of stimulation when the atrial rate exceeds a predetermined upper tracking rate.

As described earlier, use of short AV delay during the CTS as well as during the above-mentioned state of the ACC feature is an attempt to ensure that the ventricular pace pulse is delivered well before any conducted intrinsic event can occur in the ventricle. When using the known Wenckebach method for atrium-synchronous stimulation of the ventricle wherein a ventricular stimulation pulse is delayed until it no more violates an Upper Tracking Rate limit thus exceeding the used short AV-delay from time to time, the chances of getting fusion beats increase in spite of the intended use of the short AV delay. To avoid this, the prior art method forces the known Ratio method for tracking in the ventricle—this method simply aborts the delivery of a ventricular stimulation pulse if it violates the Upper Tracking Rate limit. However, with such approach, an undesirable behavior of extended period of ventricular sense sequence, which is triggered by a backup stimulation pulse, can occur. This is particularly undesirable for CRT patients.

To address the above-described problem, it is suggested to use the known Wenckebach mode of scheduling ventricular stimulation pulses with the added check to see whether or not a delivered ventricular stimulation pulse was delayed beyond the intended short AV delay. In case of a delayed pulse delivery, an immediate—or, as soon as possible—delivery of a backup pulse is suggested without performing any capture analysis. Since no capture analysis is to be performed for such pulses, the heart stimulator preferably ignores the result of capture analysis following such ventricular stimulation pulses during CTS and ACC.

Another further problem is directed to the delivery of ventricular stimulation pulses at the end of a safety window.

As described earlier, the ACC feature allows use of a low safety margin above the capture threshold since a backup pulse is delivered in case capture analysis of the post-pace artifact reveals a non-capture. Traditional bradycardia support modes include a feature called Safety Window Pacing (SWP) when working in a dual-chamber pacing mode. Basically, if a ventricular sense event is detected soon after the delivery of an atrial stimulation pulse, a delivery of a ventricular stimulation pulse is enforced at the end of the Safety Window. The reason for doing so is that the ventricular sense event can be a genuine ventricular depolarization or it can as well be detection of crosstalk due to the atrial pace pulse. Due to the low safety margin in use, the ventricular stimulation pulse at the end of the Safety Window also runs the risk of not producing a capture—however, it is not recommendable to deliver a backup pace pulse in this case as the backup pulse may come too late in case of a genuine sense event, and, thus, risk triggering an arrhythmia.

As a solution to this problem, it is suggested to use a ventricular stimulation pulse of higher pacing energy—preferably same as what is used in the backup pulses—for Safety Window Pacing.

Yet another problem refers to initialization of the ACC feature.

The reliability of the outcome of the capture analysis also depends on the post-pace artifact that is presented to the lead system and the sensing stage of the heart stimulator. If this artifact is too large during an expected case of non-capture, the capture analysis cannot lead to reliable conclusions. At the time of the initialization of the ACC feature, the post-pace artifact is measured for non-capturing pace events and the feature is disabled in case of too large artifacts. However, immediately following a lead implant, the post-pace artifact can be extra large due to the so-called injury potential. As a result, the ACC feature is disabled. The artifact may come down to reasonable value after a few weeks—however, it requires another follow-up visit before the feature can be initialized again by the attending physician.

As a solution to the latter problem, it is suggested that the heart stimulator is adapted to automatically repeat initialization of the ACC feature at programmed periods, e.g. every two weeks, until the ACC feature can be activated. Preferably, the total number of initialization attempts should be limited by a programmable count.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
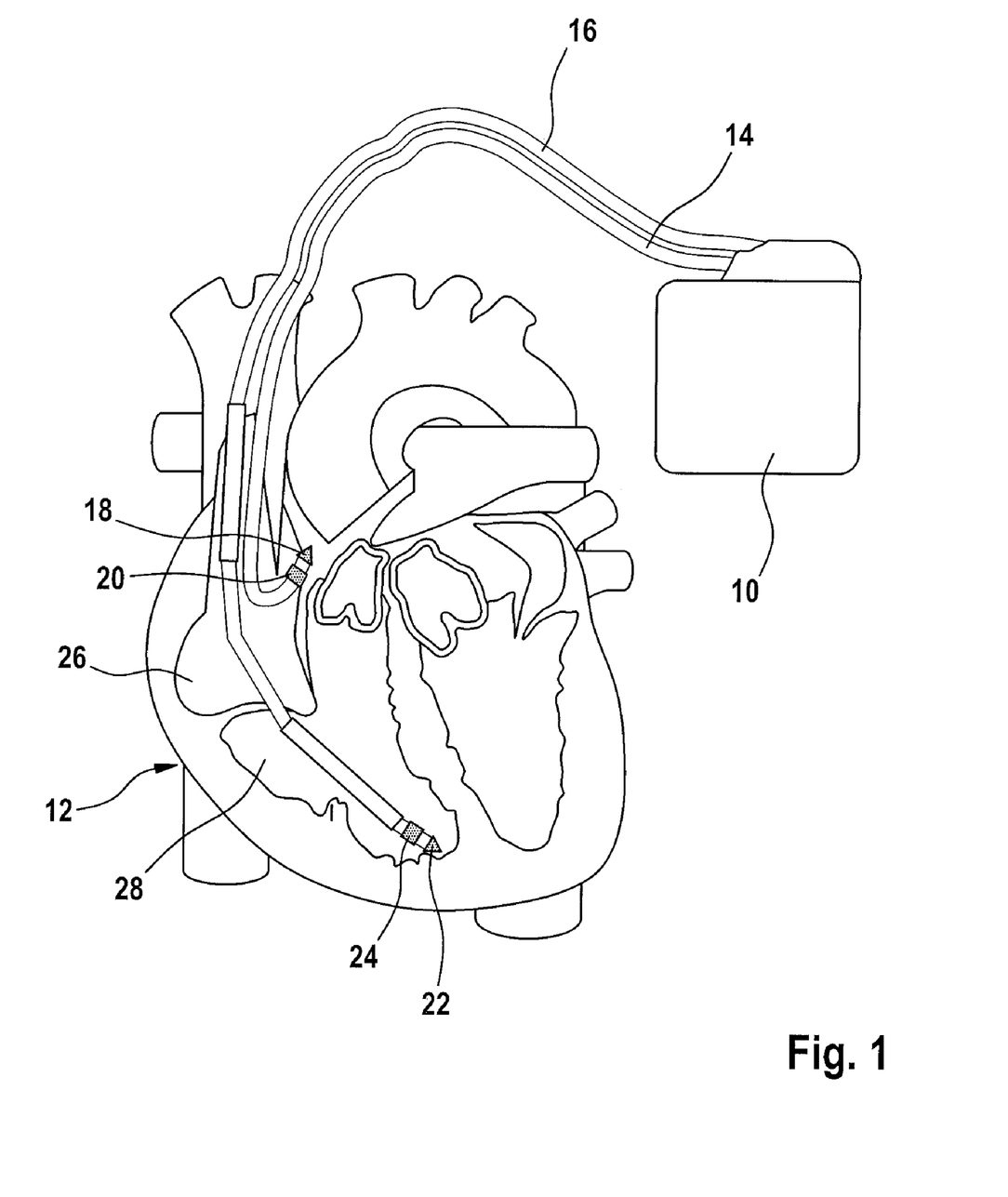
FIG. 1 shows a dual chamber pacemaker connected to leads placed in a heart.

In FIG. 1 a dual chamber pacemaker 10 as heart stimulator connected to pacing/sensing leads placed in a heart 12 is illustrated. The pacemaker 10 is electrically coupled to heart 12 by way of leads 14 and 16. Lead 14 has a pair of right atrial electrodes 18 and 20 that are in contact with the right atria 26 of the heart 12. Lead 16 has a pair of electrodes 22 and 24 that are in contact with the right ventricle 28 of heart 12. Electrodes 18 and 22 are tip-electrodes at the very distal end of leads 14 and 16, respectively. Electrode 18 is a right atrial tip electrode RA-Tip and electrode 22 is a right ventricular tip electrode 22. Electrodes 20 and 24 are ring electrodes in close proximity but electrically isolated from the respective tip electrodes 18 and 22. Electrode 20 forms a right atrial ring electrode RA-Ring and electrode 24 forms a right ventricular ring electrode RV-Ring.

Figure 2:
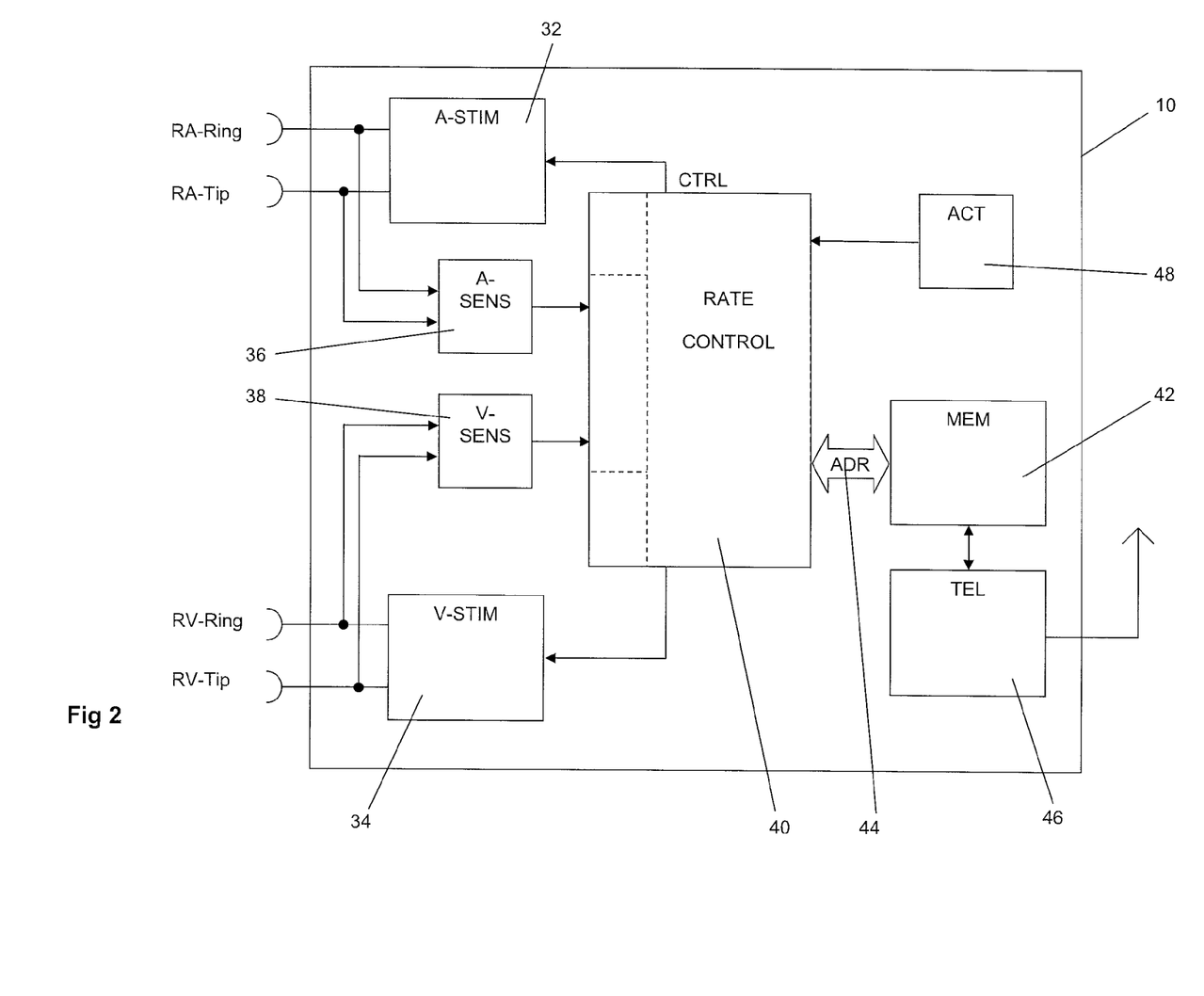
FIG. 2 is a block diagram of a heart stimulator according to the invention.

Referring to FIG. 2 a simplified block diagram of a dual chamber pacemaker 10 is illustrated. During operation of the pacemaker leads 14 and 16 are connected to respective output/input terminals of pacemaker 10 as indicated in FIG. 1 and carry stimulating pulses to the tip electrodes 18 and 22 from an atrial stimulation pulse generator A-STIM 32 and a ventricular pulse generator V-STIM 34, respectively. Further, electrical signals from the atrium are carried from the electrode pair 18 and 20, through the lead 14, to the input terminal of an atrial channel sensing stage A-SENS 36; and electrical signals from the ventricles are carried from the electrode pair 22 and 24, through the lead 16, to the input terminal of a ventricular sensing stage V-SENS 38.

Controlling the dual chamber pacer 10 is a control unit CTRL 40 that is connected to sensing stages A-SENS 36 and V-SENS 38 and to stimulation pulse generators A-STIM 32 and V-STIM 34. Control unit CTRL 40 receives the output signals from the atrial sensing stage A-SENS 36 and from the ventricular sensing stage V-SENS 38. The output signals of sensing stages A-SENS 36 and V-SENS 38 are generated each time that a P-wave representing an intrinsic atrial event or an R-wave representing an intrinsic ventricular event, respectively, is sensed within the heart 12. An As-signal is generated, when the atrial sensing stage A-SENS 36 detects a P-wave and a Vs-signal is generated, when the ventricular sensing stage V-SENS 38 detects an R-wave.

Atrial and ventricular stimulation pulse generators A-STIM 32 and V-STIM 34, respectively, are adapted to generate electrical stimulation pulses having an adjustable strength that depends on a control signal received from the control unit CTRL 40.

Control unit CTRL 40 also generates trigger signals that are sent to the atrial stimulation pulse generator A-STIM 32 and the ventricular stimulation pulse generator V-STIM 34, respectively. These trigger signals are generated each time that a stimulation pulse is to be generated by the respective pulse generator A-STIM 32 or V-STIM 34. The atrial trigger signal is referred to simply as the "A-pulse", and the ventricular trigger signal is referred to as the "V-pulse". During the time that either an atrial stimulation pulse or ventricular stimulation pulse is being delivered to the heart, the corresponding sensing stage, A-SENS 36 and/or V-SENS 38, is typically disabled by way of a blanking signal presented to these amplifiers from the control unit CTRL 40, respectively. This blanking action prevents the sensing stages A-SENS 36 and V-SENS 38 from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Furthermore, atrial sense events As recorded shortly after delivery of a ventricular stimulation pulses during a preset time interval called post ventricular atrial refractory period (PVARP) are generally recorded as atrial refractory sense event Ars but ignored.

Control unit CTRL 40 comprises circuitry for timing ventricular and/or atrial stimulation pulses according to an adequate stimulation rate that can be adapted to a patient's hemodynamic need as pointed out below.

Still referring to FIG. 2, the pacer 10 may also include a memory circuit MEM 42 that is coupled to the control unit CTRL 40 over a suitable data/address bus ADR 44. This memory circuit MEM 42 allows certain control parameters, used by the control unit CTRL 40 in controlling the operation of the pacemaker 10, to be programmably stored and modified, as required, in order to customize the pacemaker's operation to suit the needs of a particular patient. Such data includes the basic timing intervals used during operation of the pacemaker. Further, data sensed during the operation of the pacer may be stored in the memory MEM 42 for later retrieval and analysis.

A telemetry circuit TEL 46 is further included in the pacemaker 10. This telemetry circuit TEL 46 is connected to the control unit CTRL 40 by way of a suitable command/data bus. Telemetry circuit TEL 46 allows for wireless data exchange between the pacemaker 10 and some remote programming or analyzing device which can be part of a centralized service center serving multiple pacemakers.

The pacemaker 10 in FIG. 1 is referred to as a dual chamber pacemaker because it interfaces with both the right atrium 26 and the right ventricle 28 of the heart 12. Those portions of the pacemaker 10 that interface with the right atrium, e.g., the lead 14, the P-wave sensing stage A-SENS 36, the atrial stimulation pulse generator A-STIM 32 and corresponding portions of the control unit CTRL 40, are commonly referred to as the atrial channel. Similarly, those portions of the pacemaker 10 that interface with the right ventricle 28, e.g., the lead 16, the R-wave sensing stage V-SENS 38, the ventricular stimulation pulse generator V-STIM 34, and corresponding portions of the control unit CTRL 40, are commonly referred to as the ventricular channel.

In order to allow rate adaptive pacing in a DDDR or a DDIR mode, the pacemaker 10 further includes a physiological sensor ACT 48 that is connected to the control unit CTRL 40 of the pacemaker 10. While this sensor ACT 48 is illustrated in FIG. 2 as being included within the pacemaker 10, it is to be understood that the sensor may also be external to the pacemaker 10, yet still be implanted within or carried by the patient. A common type of sensor is an activity sensor, such as a piezoelectric crystal, mounted to the case of the pacemaker. Other types of physiologic sensors are also known, such as sensors that sense the oxygen content of blood, respiration rate, pH of blood, body motion, and the like. The type of sensor used is not critical to the present invention. Any sensor capable of sensing some physiological parameter relatable to the rate at which the heart should be beating can be used. Such sensors are commonly used with "rate-responsive" pacemakers in order to adjust the rate of the pacemaker in a manner that tracks the physiological needs of the patient.

Now the operation of pacemaker 10 shall be illustrated.

Control unit CTRL 40 is adapted to periodically carry out a capture threshold search wherein ventricular stimulation pulses having a varying pulse strength are delivered. If such ventricular stimulation pulse leads to capture of the heart's 12 myocardium, the stimulation pulse strength is lowered for the next ventricular stimulation pulse. If such ventricular stimulation pulse leads to non-capture of the heart's 12 myocardium, the stimulation pulse strength is increased for the next ventricular stimulation pulse until a minimum stimulation pulse strength is found that causes capture.

Capture analysis for determining whether or not a ventricular stimulation pulse has caused capture is performed by the control unit CTRL 40 by analyzing a post-pace artifact in a time course of electric potentials picked up by the ventricular sensing stage V-SENS 38 after delivery of the ventricular stimulation pulse and of expiration of a ventricular blanking period.

However, the result of capture analysis following a ventricular stimulation pulse that is preceded by more than one atrial event after the ventricular event immediately preceding the ventricular stimulation pulse is ignored with respect to capture threshold determination during the capture threshold search.

In order to determine whether or not the result of capture analysis is to be ignored, control unit CTRL 40 comprises a counter for counting all atrial events between a ventricular event immediately preceding an actual ventricular stimulation pulse and the actual ventricular stimulation pulse. If the counter value exceeds one, the result of the following capture analysis is ignored.

Figure 3:
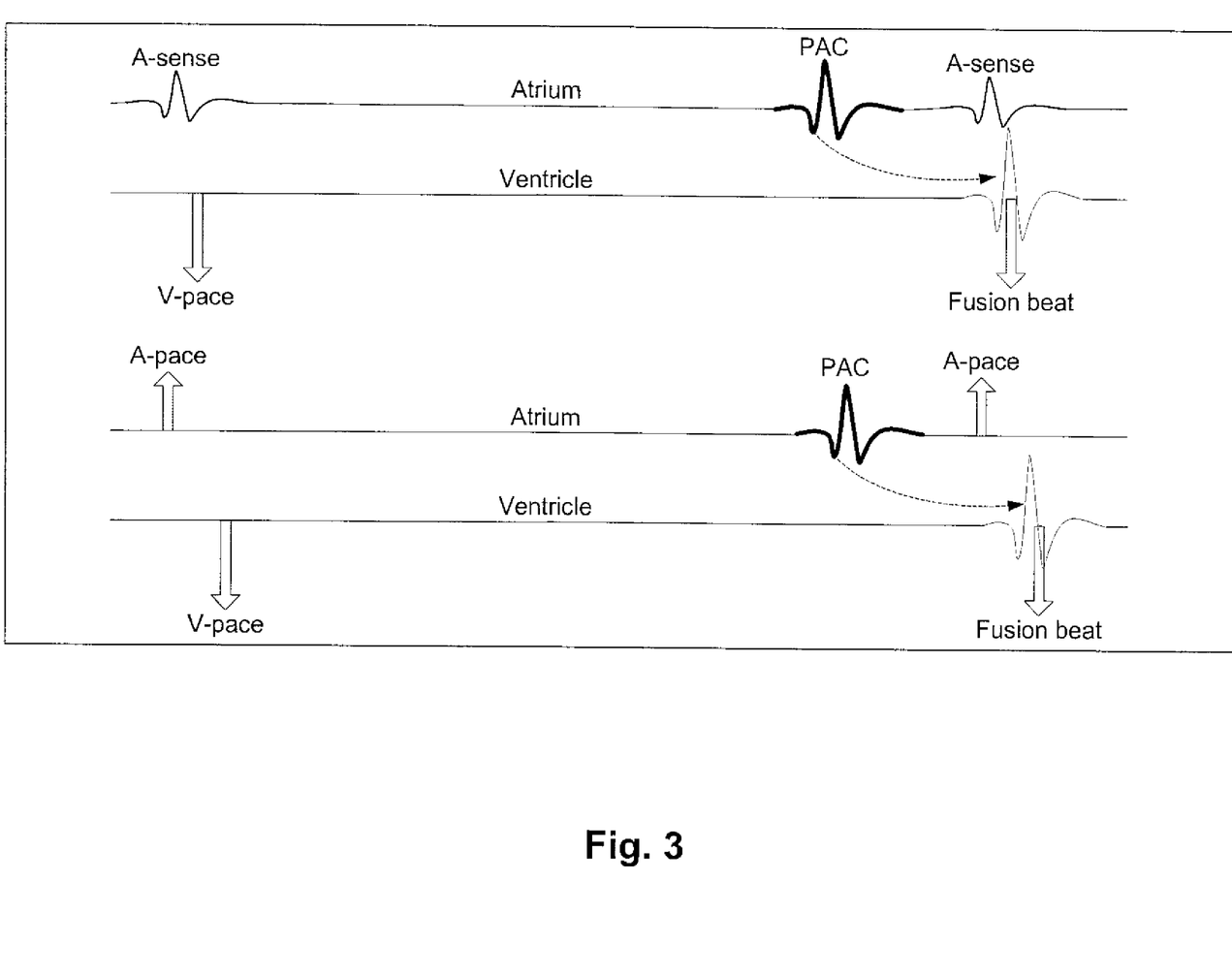
FIG. 3 is a diagram illustrating the effect of extraordinary atrial events.

In FIG. 3 it is illustrated that an extraordinary atrial event such as a premature atrial contraction PAC can lead to a fusion beat that could affect reliable capture analysis. As is apparent from FIG. 3, such PAC leads to more than one atrial event between two consecutive ventricular events.

Control unit CTRL 40 is also adapted to perform an automatic capture control ACC on a beat-to-beat basis by analyzing the post-pace artifact following every ventricular stimulation pulse.

While a capture threshold search is only carried out for a few minutes a day, automatic capture control is preferably performed permanently. Permanently applying a short AV delay attempted at avoiding fusion beats is not practical from the therapeutic point-of-view since this would suppress most intrinsic excitation of the ventricle. The risk of fusion beats causing incorrect capture analysis is, therefore, higher for the ACC feature.

Figure 4:
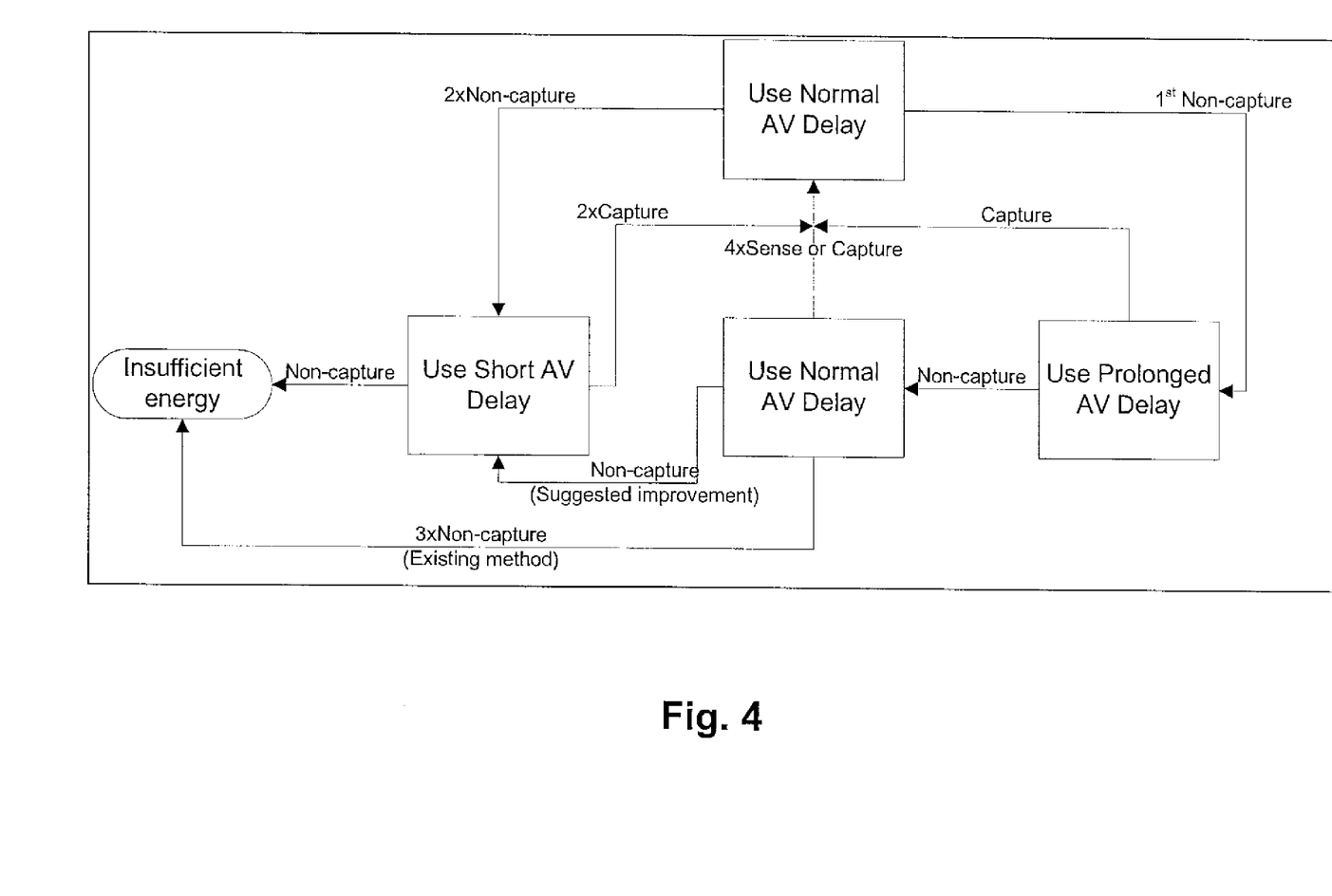
FIG. 4 is a diagram illustrating how the AV delay is altered in response to detection of non-capture outside a capture threshold search.

The behavior of pacemaker 10 during automatic capture control ACC on a beat-to-beat basis as controlled by control unit CTRL 40 is depicted in FIG. 4.

In order to cope with fusion beats during regular pacing in the ACC mode, the control unit CTRL 40 is adapted to modulate the AV delay after detection of a first non-capture in an attempt to avoid fusion beats.

The timing scheme for scheduling ventricular stimulation pulses in an atrium synchronous mode of stimulation with modulated AV-delay is illustrated in FIG. 4.

Thus, pacemaker 10 is capable of delivering stimulation pulses with the purpose of causing capture of the heart tissue and is capable of automatically verifying the results of the stimulation pulses—as to whether or not the heart tissue is being captured—on a beat-to-beat basis and, in case of non-capture, delivering backup pulses as well as confirming whether or not the non-capture analysis is resulting from fusion beats. The process of confirming the result of the capture analysis is realized by modulating the atrioventricular delay as depicted in FIG. 4, where the AV delay modulation scheme includes a step where the used atrioventricular delay is short enough to ensure that the preceding atrial event can not conduct down into the ventricle and cause a ventricular depolarization; and a declaration of insufficient energy in the stimulation pulse as a consequence of non-capture detection is made only when a non-capture detection is made using the step of short atrioventricular delay.

The process of confirming the result of the capture analysis further is capable to cope with a potential occurrence of an extraordinary atrial event, such as premature atrial contraction, with potential of producing fusion beat in the ventricle. The control unit CTRL 40 will not make changes in the AV delay or detect non-capture due to insufficient energy in the stimulation pulse following the next ventricular pace delivery if a potential occurrence of an extraordinary atrial event is detected based on the count of all atrial events that follow the preceding ventricular stimulation pulse and precede the ventricular stimulation pulse that is subject of the capture analysis. Such potential occurrence of an extraordinary atrial event is detected if the count value being higher than one.

Such heart stimulator featuring automatic capture control ACC performs a capture analysis following each delivered ventricular pace pulse. In contrast to the CTS feature that is active for brief durations, e.g. once daily for a maximum of 2 minutes, the ACC feature is active on a beat-to-beat basis. A short AV delay attempted at avoiding fusion beats is not practical from the therapeutic point-of-view. The risk of fusion beats causing incorrect capture analysis is, therefore, higher for the ACC feature. Upon detecting a first non-capture, the control unit in its ACC mode of operation modulates the AV delay in an attempt to avoid fusion beats. In prior art heart stimulators in case of continued detection of non-capture in spite of the attempts to avoid fusion beats, a confirmed case of insufficient pace energy is declared—this may lead to either a disabling of the ACC feature or start of a new CTS.

Although performing ACC according to the prior art includes a state that uses a short AV delay, that ensures that the ventricular pace pulse is delivered well before any conducted intrinsic event can occur in the ventricle, this state is not used in case of unstable rhythms where excessive number of non-captures may have been seen at other used AV delays. According to the preferred embodiment of the invention a use of the state using the short AV delay is mandatory before deciding whether or not the pace energy is insufficient.

Pacemaker 10 is further adapted to use the known Wenckebach method for ventricular tracking of the atrial activity wherein delivery of a ventricular stimulation pulse is delayed until it no longer violates the programmed Upper Tracking Rate limit. In such Wenckebach mode, control unit CTRL 40 of pacemaker 10 excludes any delayed ventricular stimulation pulse from capture analysis and also from other decision making of the feature and causes a priority delivery of a backup stimulation pulse in this case without performing any capture analysis.

Furthermore, control unit CTRL 40 is adapted to control delivery of the delayed ventricular stimulation pulse such that it has a higher stimulation strength—with higher safety margin added to the capture threshold—than ventricular stimulation pulses that are not delayed. The higher stimulation pulse strength is equal to what is used in the backup stimulation pulses.

Pacemaker 10 also is adapted to perform Safety Window Pacing (SWP) when working in a dual-chamber pacing mode. When an atrial stimulation pulse is triggered, a Safety Window is started. If a ventricular sense event is detected soon after the delivery of an atrial stimulation pulse, a delivery of a ventricular stimulation pulse is enforced at the end of the Safety Window. The Safety Window stimulation pulse has a higher stimulation pulse strength—with higher safety margin added to the capture threshold—than ordinary ventricular stimulation pulses. Also, the Safety Window stimulation pulse is not subject to any capture verification analysis. The pulse strength of the Safety Window stimulation pulse is equal to the pulse strength of backup stimulation pulses.

With respect to capture analysis—in particular during ACC—based on analysis of post-ventricular-stimulation artifact, initialization of such capture analysis feature is based on analysis of post-ventricular-stimulation artifact for pulses delivered within a window where non-capture is expected, and initialization of the capture analysis feature is only executed if the artifact is characterized to be such that it can allow capture analysis to be reliable for stimulation pulses that are intended to capture the heart tissue. A failed initialization of the capture analysis starts a delay period—programmable in units such as hours, days and weeks—after which another initialization attempt is performed; and in case of consecutive failed initialization attempts for a programmed number of count, the feature is disabled.

What is claimed is:

1. A heart stimulator for stimulating at least a ventricle of a heart comprising:
    at least one ventricular stimulation pulse generator adapted to generate electric stimulation pulses and wherein said at least one ventricular stimulation pulse generator is connected or connectable to at least one ventricular stimulation electrode configured to deliver said electric stimulation pulses to at least one ventricle of a heart, said at least one ventricular stimulation pulse generator being adapted to generate stimulation pulses that have a strength that depends on a control signal;
    at least one ventricular sensing stage connected or connectable to an electrode configured to pick up electric potentials inside said at least one ventricle of said heart wherein a time course of said electric potentials represent a heart signal; and,
    a control unit connected to said at least one ventricular sensing stage and to said at least one ventricular stimulation pulse generator wherein said control unit is adapted to
        determine points of time to schedule ventricular stimulation pulses, to trigger said at least one stimulation pulse generator so as to deliver a stimulation pulse when scheduled and to put out control signals that control stimulation pulse strength;
        perform a capture analysis after a delivery of a ventricular stimulation pulse in order to detect either capture of a stimulation pulse that was effective or non-capture of a stimulation pulse that was ineffective, said capture analysis being based on an analysis of said time course of said electric potentials as picked up by said at least one ventricular sensing stage that follows delivery of said stimulation pulse to identify an extraordinary atrial event prior to delivery of said stimulation pulse;
        identify an extraordinary atrial event prior to delivery of said stimulation pulse through a count of all atrial events that follow a previous ventricular event and that precede said ventricular stimulation pulse that is subject of said capture analysis wherein said extraordinary atrial event is identified if a counted number of atrial events exceeds one; and
        ignore a result of said capture analysis for said ventricular stimulation pulse that follows the extraordinary atrial event at least with respect to pulse strength adjustment by said control unit.

2. The heart stimulator according to claim 1, wherein said control unit comprises or is connected to an atrial event counter that is adapted to count all atrial events that follow said previous ventricular event and precede said ventricular stimulation pulse that is subject of said capture analysis.

3. The heart stimulator according to claim 1, wherein said control unit is adapted to
    carry out an automatic capture threshold test wherein ventricular stimulation pulses of varying pulse strength are delivered in an atrium synchronous stimulation mode using a shortened AV-delay being shorter than a natural atrioventricular conduction time; and,
    determine a capture threshold depending on whether a stimulation pulse of dedicated stimulation pulse strength has resulted in capture or non-capture while ignoring results following an identification of said extraordinary atrial event.

4. The heart stimulator according to claim 3, wherein said control unit is adapted to
    trigger a repeated stimulation pulse having a same pulse strength as said stimulation pulse that followed an identification of a potential extraordinary atrial event and thus was ignored with respect to capture analysis.

5. The heart stimulator according to claim 4, wherein said control unit is adapted to trigger said repeated stimulation pulse at an end of an ongoing stimulated heart cycle.

6. The heart stimulator according to claim 4, wherein said control unit is adapted to trigger said repeated stimulation pulse at an end of a next stimulated heart cycle.

7. A heart stimulator for stimulating at least a ventricle of a heart comprising:
    at least one ventricular stimulation pulse generator adapted to generate electric stimulation pulses and being connected or being connectable to at least a ventricular stimulation electrode for delivering electric stimulation pulses to said at least one ventricle of a heart, said stimulation pulse generator being adapted to generate stimulation pulses having a strength depending on a control signal;
    at least a ventricular sensing stage connected or being connectable to an electrode for picking up electric potentials inside at least said ventricle of said heart, wherein a time course of said electric potentials represent a heart signal; and,
    a control unit connected to said at least one ventricular sensing stage and to said at least one ventricular stimulation pulse generator wherein said control unit is adapted to
        determine points of time for scheduling ventricular stimulation pulses, to trigger said at least one stimulation pulse generator so as to deliver a stimulation pulse when scheduled and to put out control signals for controlling stimulation pulse strength wherein said control unit is further adapted to
        perform a capture analysis following delivery of a ventricular stimulation pulse in order to detect either capture of a stimulation pulse that was effective or non-capture of a stimulation pulse that was ineffective, said capture analysis being based on an analysis of said time course of electric potentials as picked up by said at least one ventricular sensing stage following delivery of a stimulation pulse, and to
        ignore a result of said capture analysis for said ventricular stimulation pulse that follows a preceding atrial event with an AV-delay that is longer than a predetermined short AV-delay being shorter than a natural atrioventricular conduction time.

8. The heart stimulator according to claim 7, wherein said control unit is adapted to identify an extraordinary atrial event prior to delivery of said stimulation pulse, and to ignore a result of said capture analysis for a ventricular stimulation pulse following such said extraordinary atrial event at least with respect to pulse strength adjustment by said control unit.

9. The heart stimulator according to claim 7 wherein said control unit is adapted to carry out an automatic capture control on a beat-to-beat basis.

10. The heart stimulator according to claim 9, wherein said control unit is adapted to confirm a result of said capture analysis by modulating an atrioventricular delay wherein
  an AV delay modulation scheme includes a step where an atrioventricular delay that is used is short enough to ensure that a preceding atrial event cannot conduct down into a ventricle and cause a ventricular depolarization; and,
  a declaration of insufficient energy in a stimulation pulse as a consequence of non-capture detection is made only when a non-capture detection is made using a short atrioventricular delay.

11. The heart stimulator according to claim 7, wherein said control unit is adapted to schedule triggering of ventricular stimulation pulses in a Wenckebach mode of operation, and wherein said control unit is further adapted to trigger delivery of a backup stimulation pulse following a ventricular stimulation pulse was delayed beyond expiration of said predetermined short AV-delay being shorter than said natural atrioventricular conduction time.

12. The heart stimulator according to claim 11, wherein said control unit is adapted to ignore said ventricular stimulation pulse that was delayed beyond expiration of a predetermined short AV-delay and a following backup stimulation pulse with respect to capture analysis.

13. The heart stimulator according to claim 7, wherein said control unit is adapted to perform a capture analysis after initialization of a capture analysis feature, wherein said control unit is further adapted to initialize the capture analysis feature based on analysis of post-ventricular-stimulation artifact for pulses delivered within a window where non-capture is expected, and initialization of said capture analysis feature is only executed if said post-ventricular-stimulation artifact is characterized to be such that it can allow capture analysis to be reliable for stimulation pulses that are intended to capture heart tissue.

14. The heart stimulator according to claim 13, wherein said control unit is further adapted to start a delay period when said initialization of said capture analysis feature failed after which another initialization attempt is performed; and in case of consecutive failed initialization attempts for a programmed number of count, said capture analysis feature is disabled.

15. The heart stimulator according to claim 14, wherein said delay period is programmable in units such as hours, days and weeks.

16. The heart stimulator according to claim 7 further comprising an atrial stimulation pulse generator adapted to generate electric stimulation pulses and being connected or being connectable to at least one atrial stimulation electrode for delivering said electric stimulation pulses to at least one atrium of said heart, and wherein said control unit is connected to said at least one atrial stimulation pulse generator and is adapted to determine points of time for scheduling atrial stimulation pulses, to trigger said at least one atrial stimulation pulse generator so as to deliver said atrial stimulation pulse when scheduled wherein said control unit is further adapted to start a safety window with each triggering of an atrial stimulation pulse and to trigger a ventricular safety window stimulation pulse when said safety window times out, said safety window stimulation pulse having a stronger pulse strength than a regular ventricular stimulation pulse and said safety window stimulation pulse being ignored with respect to capture analysis.

17. A method of operating a heart stimulator comprising:
  delivering scheduled ventricular electric stimulation pulses having a predetermined strength;
  picking up a time course of ventricular electrical potentials after delivery of said stimulation pulses;
  counting atrial events in a time window ending with said delivery of said ventricular electric stimulation pulse, said time window beginning with a ventricular event immediately preceding said ventricular electric stimulation pulse;
  performing capture analysis of said time course of electrical potentials to determine whether said ventricular stimulation pulse has been effective and thus has caused capture or whether said ventricular stimulation pulse has not been effective and thus led to non-capture; and,
  inhibiting capture analysis or ignoring the result of capture analysis if the number of counted atrial events exceeds one.

18. A method of operating a heart stimulator comprising:
  delivering scheduled ventricular electric stimulation pulses having a predetermined strength;
  picking up a time course of ventricular electrical potentials after delivery of said stimulation pulses;
  performing capture analysis of the time course of electrical potentials in order to determine whether the ventricular stimulation pulse has been effective and thus has caused capture or whether the ventricular stimulation pulse has not been effective and thus led to non-capture; and,
  inhibiting capture analysis or ignoring the result of capture analysis, if a duration of a time period between an atrial event that recedes the ventricular stimulation pulse and delivery of said ventricular stimulation pulse is longer than a predetermined short AV-delay that is shorter than a natural atrioventricular conduction time.

19. The method of claim 18, wherein said performing capture analysis is only inhibited or the result of capture analysis is only ignored, if a ventricular stimulation pulse was triggered in Wenckebach mode of operation and if said duration of a time period between an atrial event preceding said ventricular stimulation pulse and delivery of said ventricular stimulation pulse is longer than a predetermined short AV-delay that is shorter than a natural atrioventricular conduction time.

* * * * *